US010898382B2

(12) United States Patent
Accurso et al.

(10) Patent No.: US 10,898,382 B2
(45) Date of Patent: Jan. 26, 2021

(54) PATIENT INTERFACE DEVICE FOR OPHTHALMIC SURGICAL LASER SYSTEM

(71) Applicant: AMO DEVELOPMENT, LLC, Santa Ana, CA (US)

(72) Inventors: Roger W. Accurso, Pleasanton, CA (US); Jose L. Garcia, Fremont, CA (US); Daryl Wong, San Jose, CA (US); Hong Fu, Pleasanton, CA (US); Harvey Liu, Fremont, CA (US); Leonard R. Borrmann, Irvine, CA (US)

(73) Assignee: AMO Development, LLC, Santa Ana, CA (US)

( * ) Notice: Subject to any disclaimer, the term of this patent is extended or adjusted under 35 U.S.C. 154(b) by 252 days.

(21) Appl. No.: 15/956,676

(22) Filed: Apr. 18, 2018

(65) Prior Publication Data

US 2018/0303664 A1    Oct. 25, 2018

Related U.S. Application Data

(60) Provisional application No. 62/487,435, filed on Apr. 19, 2017.

(51) Int. Cl.
*A61F 9/009* (2006.01)
*A61F 9/008* (2006.01)

(52) U.S. Cl.
CPC .... *A61F 9/009* (2013.01); *A61F 2009/00872* (2013.01); *A61F 2009/00887* (2013.01)

(58) Field of Classification Search
CPC combination set(s) only.
See application file for complete search history.

(56) References Cited

U.S. PATENT DOCUMENTS 5,556,417 A * 9/1996 Sher ................... A61B 17/0231
                                                                  600/236
6,019,472 A    2/2000 Koester et al.
(Continued)

FOREIGN PATENT DOCUMENTS

WO    2014120990 A1    8/2014
WO    2016058931 A2    4/2016

OTHER PUBLICATIONS

International Search Report and Written Opinion for Application No. PCT/US2018/028064, dated Jul. 5, 2018, 14 pages.

*Primary Examiner* — Michael W Kahelin
*Assistant Examiner* — Shirley X Jian
(74) *Attorney, Agent, or Firm* — Johnson & Johnson Surgical Vision, Inc.

(57) ABSTRACT

A single-piece patient interface device (PI) for coupling an patient's eye to an ophthalmic surgical laser system, which includes a rigid shell, a flexible suction ring joined to a lower edge of the shell, an applanation lens, and a flexible annular diaphragm which joins the applanation lens to the shell near the lower edge of the shell. The flexible diaphragm allows the applanation lens to move relative to the shell, including to shift in longitudinal and lateral directions of the shell and to tilt. In operation, the surgeon first secures the PI to the patient's eye by hand, and then couples the laser system to the PI by lowering the laser delivery head into the PI shell. During the lowering process, the laser delivery head presses the applanation lens down relative to the PI to applanate the cornea of the eye.

19 Claims, 3 Drawing Sheets

(56) References Cited

U.S. PATENT DOCUMENTS

| | | | |
|---|---|---|---|
| 7,611,507 B2* | 11/2009 | Raksi | A61F 9/009 606/4 |
| 8,845,624 B2* | 9/2014 | Raksi | A61F 9/009 606/4 |
| 9,089,401 B2 | 7/2015 | Raksi et al. | |
| 9,968,486 B2* | 5/2018 | Gooding | A61F 9/00825 |
| 2007/0093796 A1* | 4/2007 | Raksi | A61F 9/009 606/10 |
| 2007/0173791 A1* | 7/2007 | Raksi | A61F 9/009 606/4 |
| 2008/0071254 A1 | 3/2008 | Lummis et al. | |
| 2010/0274228 A1 | 10/2010 | Mrochen et al. | |
| 2011/0071524 A1* | 3/2011 | Keller | A61F 9/0079 606/45 |
| 2011/0319873 A1* | 12/2011 | Raksi | A61F 9/009 606/1 |
| 2012/0016349 A1* | 1/2012 | Brownell | A61F 9/009 606/4 |
| 2013/0103014 A1 | 4/2013 | Gooding et al. | |
| 2014/0330259 A1 | 11/2014 | Raksi et al. | |
| 2015/0313465 A1* | 11/2015 | Graham | A61B 3/117 351/219 |
| 2017/0281407 A1 | 10/2017 | Garcia et al. | |

* cited by examiner

PATIENT INTERFACE DEVICE FOR OPHTHALMIC SURGICAL LASER SYSTEM

CROSS-REFERENCES TO RELATED APPLICATIONS

This application claims priority to U.S. Provisional Patent Application No. 62/487,435, filed on Apr. 19, 2017, which is incorporated herein by reference in its entirety.

BACKGROUND OF THE INVENTION

Field of the Invention

Embodiments of this invention generally relate to ophthalmic surgical laser systems, and particularly to a patient interface device used to stabilize the patient's eye and to deliver the laser beam to the eye during ophthalmic surgery, as well as related methods.

Description of Related Art

Significant developments in laser technology have led to its application in the field of ophthalmic surgery, and laser surgery has become the technique of choice for ophthalmic surgical applications. Ophthalmic surgery is a precision operation and requires precise coupling between the surgical tool (i.e., the laser beam) and the region to be surgically altered (i.e., a portion of the patient's eye). Movement of the eye with respect to the intended focal point of the laser beam can lead to non-optimal results and could even result in permanent damage to tissue within the eye. Given that eye movement is often the result of autonomic reflex, techniques have been developed in an attempt to stabilize the position of a patient's eye with respect to an incident laser beam.

Mechanical stabilization devices, referred to as patient interfaces (PI), have been developed for coupling the patient's eye to the laser system. A PI typically has a component that directly contacts the eye, and engages and stabilizes the eye; meanwhile, the PI is attached to the laser system, so that the laser beam can be aligned to the eye. Conventional designs of PIs typically have either a one-piece or a two-piece structure.

Using a two-piece structure, the user (surgeon) installs a lens cone having an applanation lens on the laser system, and installs a suction ring assembly on the patient's eye using a suction force, and then docks the two pieces together using the motorized gantry of the laser system. Two-piece structures allow the surgeon to manipulate the suction ring to fit difficult eye geometries such as small eye fissures, deep set eyes, etc., since the suction ring assembly is a stand-alone piece held in the surgeon's hand and thus free to move in any direction. In particular, the suction ring assembly can be angled and moved around to tuck under eyelids and avoid the patient's nose bridge and brow ridge prior to applying suction. As the PI is properly docked, the applanation lens is in contact with the eye and typically flattens the eye to the shape of the applanation lens during surgery.

In a one-piece structure, the lens cone having the applanation lens and the suction ring assembly are integrated as one piece. The PI is first attached to the laser system gantry, and then docked to the eye by moving the gantry in the X, Y and Z directions. The inability to move the suction ring in other degrees of freedom can make it more difficult to correctly dock the PI to the patient's eye. In some conventional system, this issue is mitigated somewhat because the diameter of the PI is small and the suction ring touches only the cornea so it is not as difficult to dock to the eye. Some other conventional systems address this issue by utilizing an articulated laser beam delivery head, to which the one-piece PI is attached. The beam delivery head is designed in such a way as to allow X, Y, Z and rotational degrees of freedom that the surgeon can use to aid docking.

Commonly-owned U.S. Pat. Appl. Pub. No. 2012/0016349 describes a PI having a two-piece structure. PCT Application Publication No. WO2014120990A1 shows a patient interface in which the contact element that contacts the eye can accommodate a small amount of deformation. U.S. Pat. No. 9,089,401 describes a PI which includes, among other things, a connector that couples the PI to the laser optical system and is configured to accommodate adjustment of the contact element of the PI, where the connector may include a flexible element, an elastic element, a magnetic coupling element, a vacuum-suction element, a gravitational connector, a frictional connector or a viscous connector.

SUMMARY

Embodiments of the present invention are directed to a patient interface device and related method that substantially obviate one or more of the problems due to limitations and disadvantages of the related art.

An object of the present invention is to provide a patient interface that has a simple construction and is easy and convenient to use.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve these and/or other objects, as embodied and broadly described, an embodiment of present invention provides a patient interface device for coupling an eye of a patient to an ophthalmic surgical laser system, which includes: a hollow shell formed of a rigid material; a flexible suction ring joined to a lower edge of the shell; an applanation lens located near the lower edge of the shell; and a flexible annular diaphragm, which joins the applanation lens to the shell at a location near the lower edge of the shell, wherein the flexible annular diaphragm allows the applanation lens to move relative to the shell.

Preferably, the flexible annular diaphragm allows the applanation lens to move in a longitudinal direction of the shell, to tilt, and to shift in a lateral direction of the shell. Preferably, the flexible annular diaphragm is formed of a thermoplastic elastomer having a hardness of Shore A durometer 20 to 65, and has a thickness of 0.010 to 0.160 inches.

In another aspect, an embodiment of present invention provides a method of using the above patient interface device to couple the eye of the patient to the ophthalmic surgical laser system, which includes: placing the patient interface device on the patient's eye, wherein the flexible suction ring contacts a surface of the patient's eye; applying a vacuum force via the flexible suction ring, whereby the patient interface device is secured to the patient's eye; and moving a laser delivery head of the ophthalmic laser system into the interior space of the hollow shell, wherein a bottom optical surface of the laser delivery head applies a force on the applanation lens to press it against a cornea of the patient's eye.

In another aspect, an embodiment of present invention provides a method of coupling an eye of a patient to an ophthalmic surgical laser system for laser eye surgery, which includes: providing a patient interface device, the patient interface device including a hollow shell formed of a rigid material and a flexible suction ring joined to a lower edge of the shell, the suction ring including a annular exterior portion and an annular interior portion, the exterior portion and interior portion being concentric with each other and defining an annular channel therebetween; placing the patient interface device on the patient's eye, wherein the flexible suction ring contacts a surface of the patient's eye; applying a vacuum force in the annular channel of the flexible suction ring, whereby the patient interface device is secured to the patient's eye; placing a liquid or a viscoelastic material over a surface of the eye inside the area surrounded by the suction ring; and moving a laser delivery head of the ophthalmic laser system into the interior space of the hollow shell, wherein a bottom optical surface of the laser delivery head contacts the liquid or the viscoelastic material.

In another aspect, an embodiment of present invention provides a method of coupling an eye of a patient to an ophthalmic surgical laser system for laser eye surgery, which includes: providing a patient interface device, the patient interface device including a hollow shell formed of a rigid material and a flexible suction ring joined to a lower edge of the shell, the suction ring including a annular exterior portion and an annular interior portion, the exterior portion and interior portion being concentric with each other and defining an annular channel therebetween; placing the patient interface device on the patient's eye, wherein the flexible suction ring contacts a surface of the patient's eye; applying a vacuum force in the annular channel of the flexible suction ring, whereby the patient interface device is secured to the patient's eye; and moving a laser delivery head of the ophthalmic laser system into the interior space of the hollow shell, wherein a bottom optical surface of the laser delivery head contacts and applanates a cornea of the patient's eye.

It is to be understood that both the foregoing general description and the following detailed description are exemplary and explanatory and are intended to provide further explanation of the invention as claimed.

DETAILED DESCRIPTION OF PREFERRED EMBODIMENTS

Embodiments of the invention provide an apparatus and related method for interfacing an ophthalmic surgical laser system with a patient's eye using a single-piece patient interface device (PI). The PI has advantages of both conventional one-piece and two-piece PIs. The PI is a hand-held piece, which allows the surgeon the full freedom of movement to achieve docking on a large variety of patient eye geometry. It enables the surgeon to first secure the PI to the eye by hand, and then couple the laser system to the PI by moving the gantry of the laser system. The integral applanation lens and suction ring also achieve the cost advantages of a conventional one-piece PI.

Figure 1:
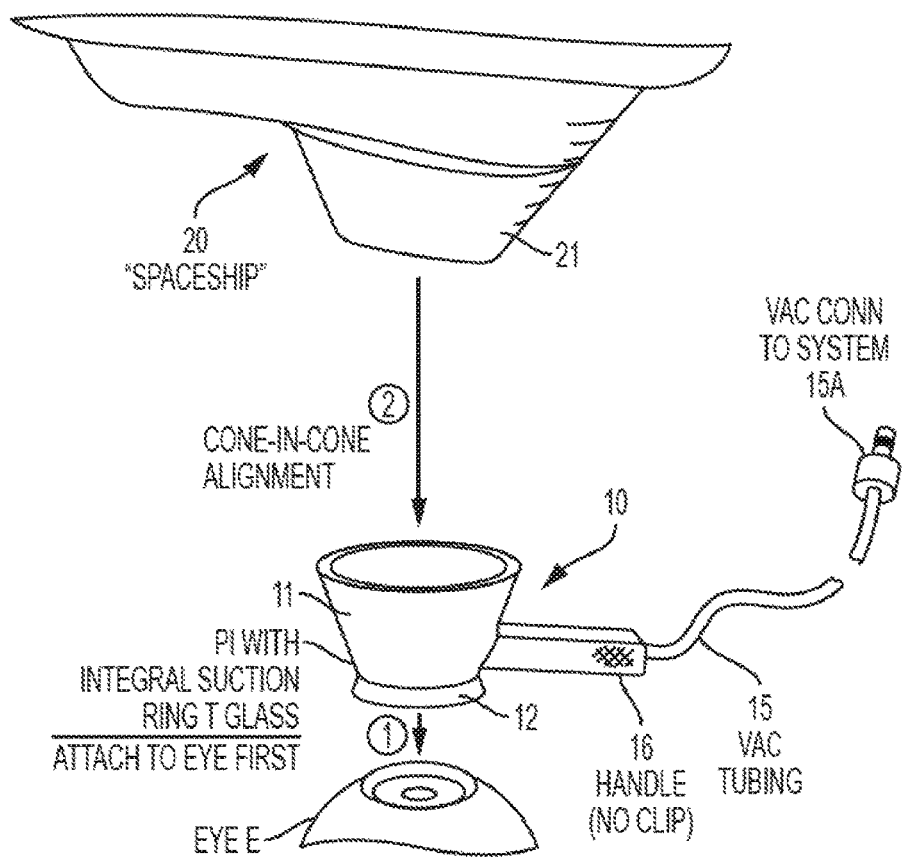
FIG. 1 is a perspective view illustrating a patient interface device (PI) and a part of the laser delivery system according to an embodiment of the present invention.
Figure 2:
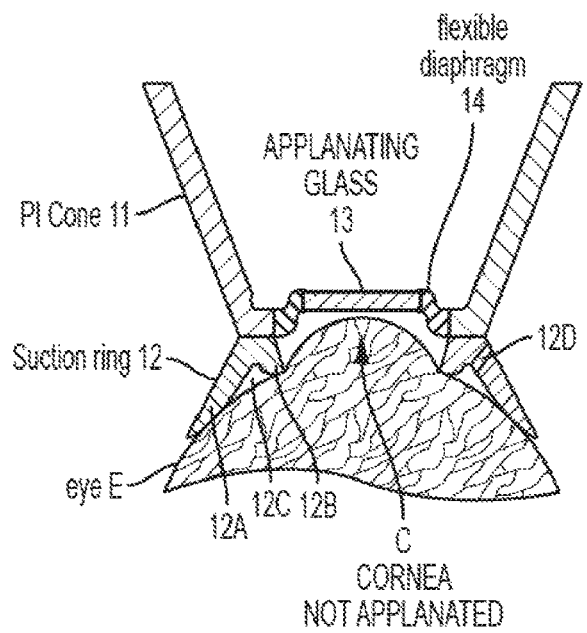
FIG. 2 is a cross-sectional view illustrating the PI coupled to a patient's eye.
Figure 3:
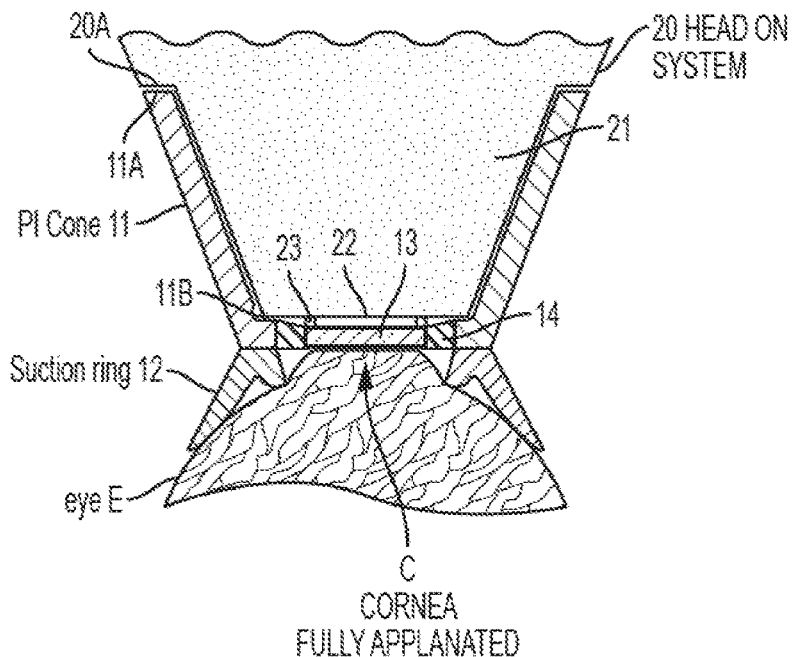
FIG. 3 is a cross-sectional view illustrating the PI coupled to a patient's eye with the laser delivery head in place.

A PI according to embodiments of the present invention is described in more detail with reference to FIGS. 1-3. The PI 10 includes a hard hollow shell 11, formed of a rigid material and preferably having an interior shape of an upside-down truncated cone, a soft and flexible suction ring 12 joined to the lower edge of the shell for coupling the PI to the patient's eye by vacuum pressure, and an applanation lens 13 located near the lower edge of the shell. The applanation lens 13 is mounted to the lower part of the shell 11 via a flexible annular diaphragm 14, which joins the applanation lens to the shell and allows the applanation lens to "float" relative to the shell 11, including to move in the longitudinal direction of the PI (the vertical direction of FIG. 2), to tilt, and to shift laterally (i.e. perpendicular to the longitudinal direction). As will be described later, this freedom to float facilitates the eye-docking procedure in which the PI is coupled to the patient's eye before it is docked with the head of the laser delivery system.

The hard shell 11 may be made of any suitable material, such as plastic, metal, etc. Note that the shell 11 does not need to have a solid side wall; it may have openings on the side wall, or it may be formed of a top ring and a bottom ring and a set of support struts extending between the top and bottom rings.

In the illustrated embodiment, the applanation lens 13 is flat on both of its surfaces, but it may also have a non-flat shape for either or both surfaces; for example, it may have a concave top surface and a flat bottom surface, or a flat top surface and a concave bottom surface, etc. When the applanation lens is concave on the bottom surface, it may be used to shape the cornea into a desired shape for the laser procedure. The applanation lens 13 is preferably made of glass, but it may also be made of other suitable materials such as transparent plastics.

The diaphragm 14 is preferably formed of a thermoplastic elastomer (TPE), or other suitable elastic materials. A large variety of commercially available materials may be used. The mechanical properties of the diaphragm 14 is designed so that it holds the applanation lens in place when no force is applied to the applanation lens, but allows the applanation lens to move within a certain range, in particular to move in the longitudinal direction and to tilt, when a force is applied to it by the cornea and/or by the laser delivery head. The stiffness of the diaphragm is a function of its material hardness and its shape, including thickness. In preferred embodiments, the diaphragm is made of a material with a hardness of Shore A durometer 20 to 65, and has a thickness of about 0.010 to 0.160 inches. The size of the diaphragm may be determined by practical considerations such as the desired size of the applanation lens 13 and the size of the suction ring 12.

The diaphragm 14 may be formed integrally with the shell 11 using overmolding techniques, or it may be formed separately by molding and then bonded to the shell using a suitable adhesive material. Note that the diaphragm 14 does not need to be a solid ring; it may have slits or cutouts, in the radial and/or circumferential directions. Such slits and cutouts may be designed to help achieve desired mechanical properties of the diaphragm.

The suction ring 12, which is designed to be affixed to a corneal portion C of the eye E by a suction force, includes annular, concentric exterior portion 12A and interior portion 12B defining an annular channel 12C between them. The lower portion of the exterior portion 12A and the lower portion of the interior portion 12B form flexible skirts, each of which functions to come into intimate contact with the anterior portion of the human eye E. The flexible skirt portions have a relatively thin cross-section and are deformable so as to establish and maintain conformal contact with the anterior corneal surface. The upper portions of the exterior portion 12A and the interior portion 12B have a structure that can maintain their shape against deformations of the lower skirt portions in response to pressure against the lower skirt portions by the human eye E. An orifice 12D that opens to the annular channel 12C is provided on the exterior portion 12A or another portion of the suction ring to provide air communication between the annular channel and a vacuum tubing 15. The vacuum tubing 15 is joined to and preferably extends radially away from the suction ring; the other end 15A of the vacuum tubing 15 is adapted to be coupled to a vacuum source. When the suction ring 12 is placed on the surface of the patient's eye E, such that the lower portions of the exterior portion 12A and interior portion 12B are in contact with the surface of the eye, the annular channel 12C is sealed, and a vacuum applied to the annular channel via the vacuum tubing 15 generates a vacuum sealing force that securely attaches the suction ring 12 to the eye. Various designs of suction rings for patient interfaces are known; for example, the above-mentioned U.S. Pat. Appl. Pub. No. 2012/0016349 describes some exemplary suction ring structures (see, for example, FIGS. 5, 6 and 11 of that application). Any suitable suction ring structure may be used in embodiments of the present invention.

The PI 10 optionally includes a handle 16 joined to the side of the shell 11 to aid in handling of the PI. A portion of the vacuum tubing may be attached to or integrated within the handle 16.

The gantry 20 of the laser system has a head portion 21, referred to as the laser delivery head, which has an exterior shape that matches the interior shape of the PI shell 11, for example, an upside-down truncated cone shape. When the gantry 20 is docked to the PI 10, the laser delivery head 21 is located inside the PI shell 11 with a fit that prevents it from moving sideways inside the PI shell, and a bottom end of the laser delivery head presses on (either directly or via a spacer structure described below) the applanation lens 13.

Note that when the exterior shape of the laser delivery head 21 is said to match the interior shape of the PI shell 11, it is meant that their shapes prevent the laser delivery head from moving sideways inside the PI shell when the laser delivery head is fully placed inside the PI shell. It does not mean that the exterior shape of the laser delivery head and the interior shape of the PI shell must be identical. Also, structural features may be provided on the laser delivery head 21 and the PI shell 11 to allow the laser delivery head to contact the PI shell to define a "fully inserted" position. For example, the gantry 20 may have a step feature 20A that contacts the top edge 11A of the PI 11 when the laser delivery head is fully inserted into the PI shell. Or, the PI shell 11 may have a step feature 11B in its interior, and a part of the laser delivery head 21 contacts this step feature when the laser delivery head is fully inserted into the PI shell. Other alternative structural features may be provided.

The bottom end of the laser delivery head 21 preferably has a flat optical surface 22 from which the laser light exits, although non-flat surfaces may also be used, especially when the applanation lens 13 has a non-flat top surface.

A spacer structure 23 is provided between the bottom surface 22 of the laser delivery head 21 and the top surface of the applanation lens 13 to form a thin air gap between these two surfaces when the laser system is docked to the eye. In a preferred embodiment, the spacer 23 includes a plurality of small beads; in other embodiments, the spacer may be a ring or other shapes. The location of the spacer 23 is selected to avoid a central area of the optical surface 22 where the laser beam passes through. The spacer 23 is formed of a hard material that will have negligible deformation when the bottom surface 22 of laser delivery head presses down on the applanation lens 13 via the spacer to applanate the cornea. The spacer 23 may be affixed to the bottom optical surface 22 by a suitable adhesive, or formed integrally on the bottom optical surface. Alternatively, the spacer 23 may be attached to or formed integrally on the top surface of the applanation lens 13.

When the laser system is docked to the eye, the applanation lens 13 is pressed from below by the patient's eye and from above by the laser delivery head 21 via the spacer 23. In such a state, the spacer 23 defines a precise, thin spacing (air gap) between the applanation lens 13 and the bottom optical surface 22 of the laser delivery head. The thickness of the air gap is preferably 25 µm to 200 µm. By precisely controlling the thickness of the air gap and the thickness of the applanation lens 13, where the latter can typically be controlled to within ±5 or even smaller tolerance, the treatment depth, i.e. the depth of the laser focus point from the surface of the cornea, can be precisely controlled. This precision control of the air gap is made possible by the spacer 23 and the flexible diaphragm 14 which allows the applanation lens 13 to float so as to conform to the position of the optical surface 22. Note that the flexible diaphragm 14 does not determine the alignment of the various parts in the docked position; the laser delivery head 21 and the spacer 23 do. The diaphragm is sufficiently soft and flexible to allow the applanation lens 13 to conform to the position requirement imposed by the laser delivery head 21 and the spacer 23.

The position of the applanation lens 13 in the "free" state, i.e., when no external force is applied on the applanation lens 13 by the eye or the laser delivery head 21, is not critical. The as-formed shape of the flexible diaphragm 14 may be such that in the free state the applanation lens 13 is held at a location near its position in the docked state, or above (see the example shown in FIGS. 2 and 3) or below such a position.

Figure 4:
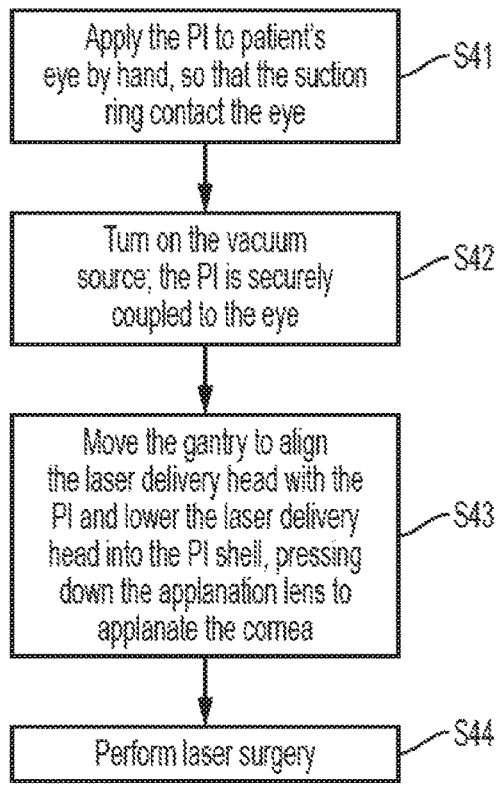
FIG. 4 schematically illustrates a docking process using the PI of FIGS. 1-3 according to an embodiment of the present invention.

In operation, the PI 10 is used to dock the patient's eye to the laser system as follows. Referring to FIG. 4, the user (surgeon) applies the PI to the patient's eye (which generally faces upward) by hand, manipulating it as needed for the patient's eye geometry (step S41). The flexible skirt portions of the suction ring 12 contact the eye (e.g. the sclera). The end 15A of the vacuum tubing is connected to a vacuum source, either before or after applying the PI to the eye. The user then turns on the vacuum source to apply a vacuum pressure to the annular channel 12C of the suction ring, so that the suction ring 12, and hence the PI 10, is securely coupled to the eye (step S42).

Preferably, the PI is designed such that in this state, i.e. after the PI is secured to the eye and before the laser delivery head is placed into the PI shell, the applanation lens does not applanate the cornea appreciably. For example, in the example shown in FIGS. 2 and 3, the as-formed shaped of the flexible diaphragm is such that it holds the applanation lens at a position above the cornea before the laser delivery head is coupled to the PI. In an alternative embodiment, the as-formed shape of the flexible diaphragm holds the applanation lens at a position such that, after the PI is secured to the eye and before the laser delivery head is placed into the PI shell, the applanation lens presses against the cornea and applanates it to a certain extent.

Then, the user moves the gantry of the laser system, which has at least three degrees of freedom of movement in the X, Y, and Z directions, to approximately align the laser delivery head 21 with the PI that has been attached to the patient's eye, and lowers the gantry 20 so that the laser delivery head 21 is placed inside the PI shell 11 (step S43). Preferably, the gantry is lowered until a part of the laser delivery head 21 contacts a part of the PI shell 11 (e.g., upper edge 11A, step feature 11B). As mentioned earlier, the laser delivery head 21 has a shape that matches the interior shape of the shell 11, such that when the laser delivery head 21 is fully lowered into the PI shell 11, the laser delivery head 21 and the shell 11 have a pre-defined spatial relationship. As the gantry is moved down, the laser delivery head 21 applies a proper amount of force, via the spacer 23, to push the floating applanation lens 13 against the cornea to applanate the cornea. Once the laser delivery head and the PI are properly docked, the system is ready to proceed with the laser surgery (step S44). The vacuum is continuously applied throughout the laser surgery.

In summary, a feature of the above-described docking procedure according to embodiments of the present invention is that a single-piece PI is used, and the unattached PI is secured to the patient's eye by hand first, before it is coupled to the laser delivery head. This provides the surgeon full freedom to manipulate the PI prior to docking it to laser system. Such a docking procedure using a single-piece PI is enabled by the fact that the applanation lens can float relative to the PI shell due to the flexible diaphragm and therefore conform to the position of the optical surface of the laser delivery head.

In alternative embodiments, modification may be made to the structure of the single-piece PI while still allowing the above described docking procedure. One modification is to eliminate the applanation lens (and hence the flexible diaphragm), but use a volume of liquid or transparent viscoelastic material as an interface between the eye surface and the bottom optical surface of the laser delivery head 21. In operation, the single-piece PI is placed on the patient's eye and secured by vacuum force; at this time, the surface of the eye is exposed to the interior of the PI due to the lack of the applanation lens, and the liquid or viscoelastic material is applied over the surface of the eye inside the area surrounded by the suction ring. Then, the laser delivery head 21 is lowered into the PI shell 11, to an appropriate vertical position, so that the space between the bottom optical surface 22 and the eye surface is filled with the liquid or material. In a further modification, where the applanation lens and the diaphragm are eliminated, no liquid or viscoelastic material is used, and the bottom optical surface 22 of the laser delivery head directly applanates the cornea. Both of these modified procedure allows for a single-piece PI to be secured to the eye first and then be docked to the laser system. Using these modified procedures, however, because the bottom optical surface of the laser delivery head contacts the eye or the liquid or viscoelastic material, the surface will need to be cleaned for each patient.

Figure 5:
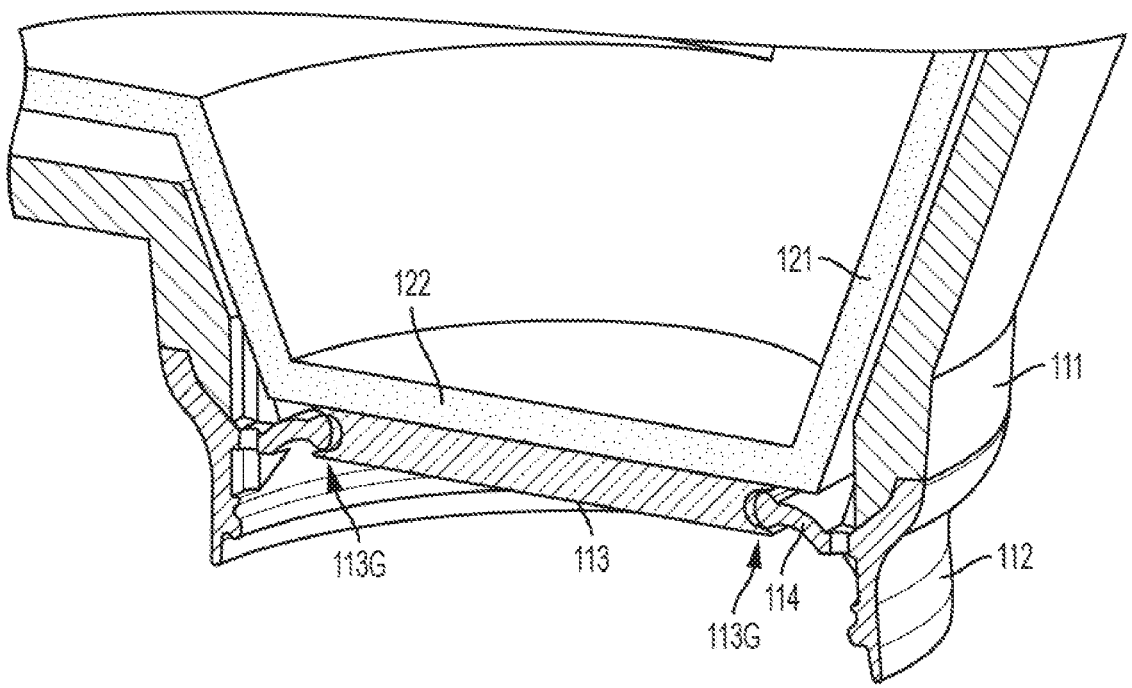
FIG. 5 is a perspective cut-away view illustrating a patient interface device and a part of the laser delivery system according to an alternative embodiment of the present invention.

FIG. 5 is a perspective cut-away view illustrating a patient interface device and a part of the laser delivery system according to an alternative embodiment of the present invention. In this alternative embodiment, the flexible diaphragm 114 and the flexible suction ring 112 are formed integrally as one piece of the same material, and joined to the lower edge of the rigid shell 111. Other aspects of the PI of FIG. 5 and its use are the same as or similar to that of the embodiments of FIGS. 1-4. Note that FIG. 5 does not show spacers between the applanation lens 113 and the bottom surface 122 of the laser delivery head 21, but such spacers may be provided in this alternative embodiment as well. Moreover, FIG. 5 illustrates a peripheral groove 113G on the edge of the applanation lens 113 which allows the inner edge of the flexible diaphragm 114 be partially inserted into the groove to hold the applanation lens 113. Such a structure may also be provided in the embodiment of FIGS. 1-3.

In additional embodiments, the PI shell 11/111 is formed of a transparent material such as lass, polycarbonate, or acrylic, where the PI shell serves as a light guide to transmit an illumination light. The illumination light is provided from the top of the PI shell 11/111 and exits the PI shell at its bottom to illuminate the eye. In this regard, a part of the bottom portion of the PI shell 11/111 may be exposed, i.e., not covered by either the suction ring 12/112 or the flexible diaphragm 14/114, to allow the light to shine onto the eye. In various ophthalmic procedures, illumination of the eye is required to form an image of the eye to aid in the procedure, or for the purpose of other optical measurements. In this embodiment, the illumination light source is integrated with the PI. Further details of such a PI integrating an illumination light source are provided in commonly owned, co-pending U.S. patent application Ser. No. 15/479,613, filed Apr. 5, 2017, which claims priority from U.S. Prov. Appl. No. 62/318,693, filed Apr. 5, 2016, both of which are incorporated herein by reference in their entireties.

The PI according to embodiments of the present invention can be used in various ophthalmic laser systems, including, without limitation, femtosecond lasers for flap cutters and laser cataract systems.

It will be apparent to those skilled in the art that various modification and variations can be made in the patient interface device and the laser delivery system as well as related methods of the present invention without departing from the spirit or scope of the invention. Thus, it is intended that the present invention cover modifications and variations that come within the scope of the appended claims and their equivalents.

What is claimed is:

1. A patient interface device for coupling an eye of a patient to an ophthalmic surgical laser system, comprising:
   a hollow shell formed of a rigid material;
   a flexible suction ring joined to a lower edge of the shell;
   an applanation lens located near the lower edge of the shell, the applanation lens having a spacer attached to its top surface; and
   a flexible annular diaphragm, which joins the applanation lens to the shell at a location near the lower edge of the shell, wherein the flexible annular diaphragm allows the applanation lens to move relative to the shell.

2. The patient interface device of claim 1, wherein the flexible annular diaphragm allows the applanation lens to move in a longitudinal direction of the shell, to tilt, and to shift in a lateral direction of the shell.

3. The patient interface device of claim 1, Wherein the flexible annular diaphragm is formed of a thermoplastic elastomer having a hardness of Shore A durometer 20 to 65, and has a thickness of 0.010 to 0.160 inches.

4. The patient interface device of claim 1, wherein the hollow shell has an interior shape of an upside-down truncated cone.

5. The patient interface device of claim 1, wherein the applanation lens has a flat top surface.

6. The patient interface device of claim 1, wherein the suction ring includes an annular exterior portion and an annular interior portion, the exterior portion and interior portion being concentric with each other and defining an annular channel therebetween, wherein the patient interface device further comprises a vacuum tubing, and wherein the suction ring further includes an orifice which opens to the annular channel to provide air communication between the annular channel and the vacuum tubing.

7. The patient interface device of claim 1, further comprising a handle, oined to the shell.

8. The patient interface device of claim 1, wherein the spacer is formed of a plurality of heads made of a hard material.

9. The patient interface device of claim 1, wherein the flexible suction ring and the flexible annular diaphragm are formed integrally as one piece of the same material which is joined to the lower edge of the shell.

10. A method of using the patient inteiface, device of claim 1 to couple the eye of the patient to the ophthalmic surgical laser system, comprising:
    placing the patient interface device on the patient's eye, wherein the flexible suction ring contacts a surface of the patient's eye;
    applying a vacuum force via the flexible suction ring, whereby the patient interface device is secured to the patient's eye; and
    moving a laser delivery head of the ophthalmic laser system into the interior space of the hollow shell, wherein a bottom optical surface of the laser delivery head applies a force on the applanation lens to press it against a cornea of the patient's eye.

11. A patient interface device for coupling an eye of a patient to an ophthalmic surgical laser system, comprising:
    a hollow shell formed of a rigid material;
    a flexible suction ring joined to a lower edge of the shell;
    an applanation lens located near the lower edge of the shell, the applanation lens having a spacer attached to its top surface; and
    a flexible annular diaphragm which, oins the applanation lens to the shell at a location near the lower edge of the shell, wherein the flexible annular diaphragm has a plurality of cutouts.

12. The patient interface device of claim 11, wherein the flexible annular diaphragm allows the applanation lens to move in a longitudinal direction of the shell, to tilt, and to shift in a lateral direction of the shell.

13. The patient interface device of claim 11, wherein the flexible annular diaphragm is formed of a thermoplastic elastomer having a hardness of Shore A durometer 20 to 65, and has a thickness of 0.010 to 0.160 inches.

14. The patient interface device of claim 11, further comprising a handle joined to the hollow shell, wherein the hollow shell has an interior shape of an upside-down truncated cone.

15. The patient interface device of claim 11, wherein the applanation lens has a flat top surface.

16. The patient interface device of claim 11, wherein the suction ring includes an annular exterior portion and an annular interior portion, the exterior portion and interior portion being concentric with each other and defining an annular channel therebetween, wherein the patient interface device further comprises a vacuum tubing, and wherein the suction ring further includes an orifice which opens to the annular channel to provide air communication between the annular channel and the vacuum tubing.

17. The patient interface device of claim 11, wherein the spacer is formed of a plurality of beads made of a hard material.

18. The patient interface device of claim 11, Wherein the flexible suction ring and the flexible annular diaphragm are formed integrally as one piece of the same material which is joined to the lower edge of the shell.

19. A method of using the patient interface device of claim 11 to couple the eye of the patient to the ophthalmic surgical laser system, comprising:
    placing the patient interface device on the patient's eye, wherein the flexible suction ring contacts a surface of the patient's eye;
    applying a vacuum force via the flexible suction ring, whereby the patient interface device is secured to the patient's eye; and
    moving a laser delivery head of the ophthalmic laser system into the interior space of the hollow shell, wherein a bottom optical surface of the laser delivery head applies a force on the applanation lens to press it against a cornea of the patient's eye.

* * * * *